United States Patent [19]

Nielsen

[11] 4,012,384
[45] Mar. 15, 1977

[54] 7-(N-METHYL-N-ALKYLAMINO)-1,3,5-TRIAZAADAMANTANES

[75] Inventor: Arnold T. Nielsen, China Lake, Calif.

[73] Assignee: The United States of America as represented by the Secretary of the Navy, Washington, D.C.

[22] Filed: July 28, 1975

[21] Appl. No.: 599,901

[52] U.S. Cl. .............................. 260/248 NS; 44/1 R
[51] Int. Cl.$^2$ ........................................ C07D 251/72
[58] Field of Search .............................. 260/248 NS

[56] References Cited

UNITED STATES PATENTS

| 3,066,139 | 11/1962 | Radoicich | 260/242 |
| 3,575,974 | 4/1971 | Hodge et al. | 260/248 |
| 3,862,187 | 1/1975 | Mitchell et al. | 260/248 |

Primary Examiner—John M. Ford
Attorney, Agent, or Firm—R. S. Sciascia; Roy Miller; Lloyd E. K. Pohl

[57] ABSTRACT

A series of high-density 7-(N-methyl-N-alkylamino)-1,3,5 triazaadamantanes are prepared. The preparation involves first adding the alkyl group to the parent amine by reacting the amine with a suitable aldehyde and hydrogen in the presence of a platinum catalyst and then reacting the thus produced secondary amine with formaldehyde and hydrogen in the presence of a nickel catalyst to produce the final product. The series represents a new class of fuels which is particularly useful in volume-limited applications.

2 Claims, No Drawings

7-(N-METHYL-N-ALKYLAMINO)-1,3,5-TRIAZAADAMANTANES

BACKGROUND OF THE INVENTION

1. Field of the Invention

This invention relates to certain adamantanes, to methods for their synthesis and to their use as fuels, especially in volume-limited applications.

2. Description of the Prior Art

For volume-limited applications such as in air-breathing long-range cruise missiles and as the fuel component of bipropellant engines in rockets and space vehicles, the ideal fuel would have high density in order to provide for maximum range for a given fuel volume. It would also have a high heat of combustion and a high specific impulse. The ideal fuel would still further be easily ignited and reignited and stable to combustion. In situations where a liquid fuel was desired, the ideal fuel would have low viscosity, be liquid in at least the range of from about −54° to about 74° and would have low vapor pressure. Still further, the ideal fuel, whether liquid or solid, would be stable during storage, corrosion resistant and of low toxicity. Finally, the ideal fuel would be low in cost. No one fuel, of course, has all of the above properties.

In the past, hydrocarbon fuels, because they have high heats of combustion, have found wide use. However, for volume-limited applications hydrocarbon fuels have certain drawbacks. High density hydrocarbons (about 1.1 g/cc or greater) are expensive. Furthermore, high density hydrocarbons generally have rather high melting points and high viscosities. Bipropellant systems utilizing hydrocarbons are usually not hypergolic (do not ignite spontaneously when the fuel and oxidizer are brought together). Hydrocarbons generally have rather low specific impulses. Since hydrocarbons represent a simple two-atom system (C, H) their potential for structural variety is limited. Last but not least, hydrocarbons are insoluble in water and, therefore, any residual water in a system which contains hydrocarbons will separate out causing fuel line freezing problems in cold weather and accelerated corrosion owing to concentration of impurities in the water.

Amine fuels, because of their great structural variety (they have a three-atom system — C, H and N), present an attractive alternate to hydrocarbons. A portion of an amine can be constructed from inexpensive, non-petroleum reactants, whereas the entire hydrocarbon is derived from petroleum. (Petroleum products are coming into ever shorter supply and will continue to do so as the World's petroleum reserves dwindle.) Most amines, and in particular, hydrazine and its derivatives, have higher specific impulses than hydrocarbons. Most bipropellant systems utilizing amines as the fuel component are hypergolic. Amine fuels, in some applications, have safety advantages over hydrocarbons. Those that are soluble in water and those that have densities greater than 1.0 g/cc may easily be extinguished in case of fire. The soluble ones simply dissolve and a burning dense amine sinks, permitting the fire to be smothered. Amines, however, like hydrocarbons have drawbacks.

One drawback of amines is that those with high density, like hydrocarbons, generally have high melting points and high viscosities (or are solids). Another drawback is that amines generally have lower gravimetric heats of combustion than hydrocarbons. These and other drawbacks have provided cause for continued experimentation in efforts to find materials with more good and less bad properties. Stated another way, the search goes on in efforts to find amines (or hydrocarbons or other materials) which are more suitable for use as fuels than those presently in use.

SUMMARY OF THE INVENTION

According to this invention, a series of 7-(N-methyl-N-alkylamino)-1,3,5-triazaadamantanes which are suitable for use as fuels are prepared. The synthesis involves preparing 7-nitro-1,3,5-triazaadamantane by adding nitromethane and paraformaldehyde to a refluxing solution of ammonium acetate and ethanol, preparing 7-amino-1,3,5-triazaadamantane by reacting the nitro derivative with hydrogen in the presence of rhodium-charcoal catalyst, preparing 7-(N-alkylamino-1,3,5-triazaadamantane by reacting the amino derivative with a suitable aldehyde and hydrogen in the presence of a platinum catalyst and, finally, preparing 7-(N-methyl-N-alkylamino)-1,3,5-triazaadamantane by reacting the N-alkylamino derivative with formaldehyde and hydrogen in the presence of a nickel catalyst. The amines of this invention are solids at room temperature and may be utilized as solid fuels. Also, they are soluble in a wide variety of hydrocarbon solvents and, accordingly, can be dissolved in such solvents for use as liquid fuels. Insofar as is known by the inventor, the amines whose preparation is described herein, with the exception of 7-(N,N-dimethylamino)-1,3,5-triazaadamantane, have never been prepared before.

DESCRIPTION OF THE PREFERRED EMBODIMENT

A detailed description of the preparation of 7-(N-methyl-N-alkylamino)-1,3,5-triazaadamantanes may conveniently be provided by a series of specific examples.

EXAMPLE 1

7-Nitro-1,3,5-triazaadamantane (1)

To ammonium acetate (129 g., 1.67 moles) in 200 ml. of 95% ethanol was added, slowly with stirring, through separate necks of a 1-1 4-necked flask: (1) a solution of nitromethane (33.3 g., 0.544 mole) in 50 ml. of 95% ethanol (addition time 4 hours), and (2) paraformaldehyde (111g., 3.70 moles) (addition time 5 hours). Stirring and reflux were continued for 1 hour after addition of the formaldehyde was complete. Then the mixture was stirred at ambient temperature for 9 hours. The white crystalline product was filtered and washed with cold ethanol to yield 42.5 g. of 1, m.p. 305°–310° dec. The light orange filtrate was concentrated under reduced pressure at 90° to remove volatiles and yield 96.5 g. of a viscous oil mixed with crystals. The residue was dissolved in 100 ml. of hot 95% ethanol and chilled to 0° to yield 9.4 g. of additional 1, m.p. 290°–300° dec. (total yield 51.9 g., 52%). The isolated material is of high purity and may be used for reduction to the corresponding amine without further purification. If desired it may be recrystallized from water to yield long needles, m.p. 285°–310°.

EXAMPLE 2

7-Amino-1,3,5-triazaadamantane (2)

7-Nitro-1,3,5-triazaadamantane (46.1 g., 0.25 mole), 175 ml. of 95% ethanol and 8.0 g. of 5% rhodium-charcoal catalyst were shaken with hydrogen in a Parr apparatus at 25° until hydrogen uptake ceased (13 hours). (The reaction bottle was refilled with hydrogen at intervals as required to keep the hydrogen pressure between 25-50 psi.) The reaction mixture was filtered with suction through Celite and the collected catalyst washed thoroughly with ethanol. The filtrate was concentrated to dryness under reduced pressure and the solid residue, after being ground to a powder, was pumped at 25° and 0.1 mm for 12 hours to remove traces of volatiles to yield 38.6 g. (99.5%) of high purity 2, m.p. 216°–219°. The product may be recrystallized from benzene (80% recovery) to yield long needles, m.p. 214°–217°; nmr (deuterium oxide): δ 4.70 (2, s, OH), 4.39, 3.97 (6, ABq, J = 12 Hz; 2,4,9 $CH_2$), 3.17 (6, s, 6,8,10 $CH_2$); TMS external standard.

EXAMPLE 3

7-(Pentylamino)-1,3,5-triazaadamantane (3e)

7-Amino-1,3,5-triazaadamantane (30.8 g., 0.2 mole), pentanal (17.2 g., 0.2 mole), platinum oxide catalyst (0.7 g.) and 150 ml. of 95% ethanol were shaken with hydrogen in a Parr apparatus at 25° (initial pressure 50 psi) until hydrogen uptake ceased (1 hour). The mixture was filtered through Celite, and the residue concentrated under reduced pressure to remove ethanol. The residue was dissolved in 300 ml. of benzene and dried with Drierite at 25°. The mixture was concentrated to dryness and the residue pumped at 0.1 mm (90°) to remove volatiles leaving 43.6 g. (97%) of high purity 3e; the material may be purified by sublimation, without loss, m.p. 119°–120°; ir (Nujol): 3300 $cm^{-1}$ (NH, weak); nmr (deuteriochloroform): δ 4.44, 4.08 (6, ABq, J = 12 Hz, 2,4,9 $CH_2$), 3.29 (6, s, 6,8,10 $CH_2$), 2.56 (2, m, $CH_2N$ of $C_5H_{11}$), 1.33 [7, m, NH and $(CH_2)_3$], 0.90 (3, m, $CH_3C$).

EXAMPLE 4

7-(N-Alkylamino)-1,3,5-triazaadamantanes (3b, c, d, f, g, h)

The procedure described above for preparation of 3e was used for preparation of other 7-(N-alkylamino)-1,3,5-triazaadamantanes (3b, c, d, f, g, h) from 2 by utilizing other aldehydes (acetaldehyde, propanal, butanal, hexanal, 2-methylpropanal, and 2,3-dimethylpentanal in lieu of pentanal. Analytical samples were prepared by sublimation and/or recrystallization from hexane. Yields, melting points and elemental analyses of the new substances are summarized in Table 1. Their infrared and NMR spectra are similar to that of 3e except for the N-alkyl signals.

EXAMPLE 5

7-(N,N-Dimethylamino)-1,3,5-triazaadamantane (4a)

7-Amino-1,3,5-triazaadamantane (3.08 g., 0.020 mole) formalin (4.0 ml., 0.053 mole), 50 ml. of methanol and 1.2 g. of freshly prepared W-2 Raney nickel catalyst were shaken in a Parr apparatus at 50 psi for 4 hours. The mixture was filtered through Celite, washed with water, and the filtrate concentrated to dryness under reduced pressure. The residue was sublimed at 100° (0.1 mm) to yield 3.3 g. (91%) of 4a, m.p. 110–111°; ir (Nujol): revealed absence of NH bands.

EXAMPLE 6

7-(N-Methyl-N-pentylamino)-1,3,5-triazaadamantane (4e)

To 7-(N-pentylamino-1,3,5-triazaadamantane (3e, 44.8 g., 0.20 mole) in 100 ml. of methanol was added 16 ml. of 37% formalin (0.21 mole of formaldehyde). A slight exothermic reaction occurred causing the temperature of the solution to rise to 34°. The solution was cooled to 15° and 4.0 g. of freshly prepared Raney nickel W-2 catalyst was added. The mixture was shaken with hydrogen in a Parr apparatus until hydrogen uptake ceased (16 hours, 25°, 30–50 psi). The reaction mixture was filtered through Celite and the residue concentrated under reduced pressure to yield 47.6 g. (100%) of 4e, m.p. 30°–31°; distillation gave 43.9 g. (92%), b.p. 112°–117° (0.1 mm) (bath temp. 150°–170°), m.p. 32°–35°; ir (Nujol): reveals absence of NH absorption bands; nmr (deuteriochloroform): δ 4.34, 4.00 (6, ABq, J = 12 Hz, 2,4,9 $CH_2$), 3.33 (6, s, 6,8,10 $CH_2$), 2.37 (2, m, $CH_2N$ of $C_5H_{11}$), 2.19 (s, 3, $CH_3N$), 1.27 [6, m, $(CH_2)_3$], 0.87 (3, m, $CCH_3$).

EXAMPLE 7

7-(N-Methyl-N-alkylamino)-1,3,5-triazaadamantanes (4b, c, d, f)

The procedure employed above for preparation of 4e was used for preparation of other 7-(N-methyl-N-alkylamino)-1,3,5-triazaadamantanes (4b, c, d, f). Analytical samples were prepared by sublimation, distillation and/or recrystallization from hexane. Yields, melting points, and elemental analyses of the new substances are summarized in Table 2. Their infrared and nmr spectra are similar to that of 4e except for the N-alkyl signals.

EXAMPLE 8

7-(1-Piperidyl)-1,3,5-triazaadamantane (5)

7-Amino-1,3,5-triazaadamantane (1.54 g., 0.01 mole), 25% aqueous glutaraldehyde solution (4.0 g., 0.01 mole), 200 ml. of 95% ethanol and 0.2 g. of platinum oxide catalyst were shaken in a Parr apparatus at 25° (50 psi) until hydrogen uptake ceased (3 hours). The mixture was filtered and the filtrate concentrated to yield a white solid residue which was extracted with 40 ml. of hot hexane leaving 1.1 g. of gummy insoluble material. The extract was concentrated to remove solvents leaving 1.1 g. of crude 5, m.p. 140°–170°; recrystallization from hexane gave flat prisms (0.57 g., 26%, m.p. 160°–170°); further recrystallization gave an analytical sample, m.p. 166°–172°; ir (Nujol): revealed absence of NH bands; mnr (deuteriochloroform): δ 4.44, 4.06 (6, ABq, J = 12 Hz, 2,4,9 $CH_2$), 3.44 (6, s, 6,8,10 $CH_2$), 2.60 (4, m, $CH_2N$ of piperidyl), 1.49 (6, m, 3,4,5 $CH_2$ of piperidyl).

Anal. Calcd. for $C_{12}H_{22}N_4$: C, 64.82; H, 9.97; N, 25.20; mol. wt. 222.33. Found: C, 64.69; H, 10.15; N, 25.12; ml. wt. 218 (osomometry in chloroform).

The 7-(N-alkylamino)-1,3,5-triazaadamantanes were those having the formula:

wherein R is CH$_3$ (4a); C$_2$H$_5$ (4b); n-C$_3$H$_7$ (4c); n-C$_4$H$_9$ (4d); n-C$_5$H$_{11}$ (4e); or n-C$_6$H$_{13}$ (4f). A summary of some of their properties appears in Table 2.

Table 2

| | | | | | 7-(N-Methyl-N-alkylamino)-1,3,5-triazaadamantanes | | | | | | | |
|---|---|---|---|---|---|---|---|---|---|---|---|---|
| | | | | | Elemental Analyses | | | | | | | |
| | | Yield(a) | M.P. | Density g/cc at | Mole- cular | Calculated | | | | Found | | | |
| Cpd. | R | % | °C(b) | 208 (obs) | Formula | %C | %H | %N | Mol wt | %C | %H | %N | Mol wt(c) |
| 4a | CH$_3$ | 91 | (d)110-1-11 | 1.18 | C$_9$H$_{18}$N$_4$ | 59.30 | 9.95 | 30.74 | 182.3 | 59.53 | 9.78 | 30.84 | 181 |
| 4b | C$_2$H$_5$ | 97 | 87–89 | 1.15 | C$_{10}$H$_{20}$N$_4$ | 61.18 | 10.27 | 28.55 | 196.3 | 61.19 | 10.24 | 28.71 | 195 |
| 4c | n-C$_3$H$_7$ | 90 | 57–60 | 1.12 | C$_{11}$H$_{22}$N$_4$ | 62.81 | 10.54 | 26.64 | 210.3 | 62.65 | 10.59 | 26.48 | 207 |
| 4d | n-C$_4$H$_9$ | 98 | 35–38 | 1.10 | C$_{12}$H$_{24}$N$_4$ | 64.24 | 10.78 | 24.98 | 224.3 | 64.05 | 10.78 | 25.06 | 223 |
| 4e | n-C$_5$H$_{11}$ | 100 | 32–35 | 1.08 | C$_{13}$H$_{26}$N$_4$ | 65.50 | 11.00 | 23.51 | 238.4 | 65.28 | 10.81 | 23.34 | 243 |
| 4f | n-C$_6$H$_{13}$ | 90 | 28–30 | 1.06 | C$_{14}$H$_{28}$N$_4$ | 66.62 | 11.18 | 22.20 | 252.4 | 66.80 | 11.10 | 22.25 | 250 |

(a)Yield of unrecrystallized material obtained by reductive methylation of 3 except for 4a prepared directly from 2.
(b)M.p. of dried recrystallized (hexane), sublimed material used for elemental analysis (sealed capillary).
(c)Molecular weight determination by vapor osomometry in benzene or chloroform solutions.
(d)Lit m.p. 106–108° from E. B. Hodge, Journal of Organic Chemistry, 37, 320 (1972).

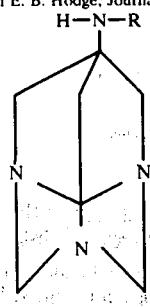

wherein R is C$_5$H$_{11}$ (3e); C$_2$H$_5$ (3b); n-C$_3$H$_7$ (3c); n-C$_4$H$_9$ (3d) ; n-C$_6$H$_{13}$ (3f); i-C$_4$H$_9$ (3g) or C$_2$H$_5$CH(CH$_3$)CH(CH$_3$)CH$_2$-(optically inactive mixture of diastereoisomers)(3h). A summary of some of their properties appears in Table 1.

The 7-dialkylamino (or, more specifically) 7-(N-alkyl-N-methylamino) derivatives of 1,3,5-triazaadamantane have properties similar to hexamethylenetetramine (an excellent fuel) but with many added advantages. They are relatively low-melting and are quite stable thermally. They may be distilled or sublimed without significant decomposition. They are quite soluble in a wide range of solvents including water, ethanol, ether and benzene (they may be recrystallized from hexane or other alkanes).

Bipropellant systems employing these amines are hypergolic; spontaneous ignition occurs with red fuming nitric acid. They have high specific impulses, high volumetric heats of combustion and high hydrogen densities. They may be easily synthesized from inexpensive reactants — 55 to 60% by weight from non- Table 1

| | | | | | 7-(N-Alkylamino)-1,3,5-triazaadamantanes | | | | | | | |
|---|---|---|---|---|---|---|---|---|---|---|---|---|
| | | | | | Elemental Analyses | | | | | | | |
| | | Yield(a) | M.P. | Molecular | Calculated | | | | Found | | | |
| Cpd. | R | % | °C(b) | Formula | %C | %H | %N | Mol wt | %C | %H | %N | Mol wt(c) |
| 3b | C$_2$H$_5$ | 98 | 126–129 | C$_9$H$_{18}$N$_4$ | 59.30 | 9.95 | 30.74 | 182.3 | 59.10 | 9.83 | 30.97 | 186 |
| 3c | n-C$_3$H$_7$ | 95 | 103–104 | C$_{10}$H$_{20}$N$_4$ | 61.18 | 10.27 | 28.55 | 196.3 | 61.34 | 10.23 | 28.53 | 195 |
| 3d | n-C$_4$H$_9$ | 99 | 112–114(d) | C$_{11}$H$_{22}$N$_4$ | 62.81 | 10.54 | 26.64 | 210.3 | 62.56 | 10.49 | 26.39 | 208 |
| 3e | n-C$_5$H$_{11}$ | 97 | 119–120 | C$_{12}$H$_{24}$N$_4$ | 62.24 | 10.78 | 24.98 | 224.3 | 64.10 | 10.75 | 24.80 | 226 |
| 3f | n-C$_6$H$_{13}$ | 93 | 118–120 | C$_{13}$H$_{26}$N$_4$ | 65.50 | 11.00 | 23.51 | 238.4 | 65.29 | 10.83 | 23.57 | 240 |
| 3g | i-C$_4$H$_9$ | 92 | 154–156 | C$_{11}$H$_{22}$N$_4$ | 62.81 | 10.54 | 26.64 | 210.3 | 62.68 | 10.53 | 26.70 | 206 |
| 3h | C$_7$H$_{15}$(-e) | 92 | 124–125 | C$_{14}$H$_{28}$N$_4$ | 66.62 | 11.18 | 22.20 | 252.4 | 66.67 | 11.27 | 22.21 | 250 |

(a)Yield of high-purity unrecrystallized material obtained by reductive alkylation of 2.
(b)M.p. of dried, recrystallized (hexane), sublimed material used for elemental analyses (sealed capillary).
(c)Molecular weight determination by vapor osomometry in benzene or chloroform solutions.
(d)Lit m.p. 103–104° from V. Galik, M. Safar, Z. Kafka and S. Landa, Collection Czechoslovak Chemical Communications, 40, 442 (1975).
(e)C$_7$H$_{15}$ = C$_2$H$_5$CH(CH$_3$)CH(CH$_3$)CH$_2$, optically inactive mixture of diastereoisomers.

The 7-(N-methyl-N-alkylamino)-1,3,5-triazaadamantanes were those having the formula:

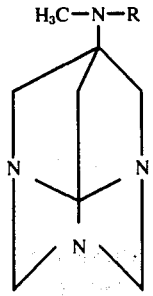

petroleum derived ammonia and formaldehyde. They are non-corrosive. They have a relatively low pour point in comparison to many high density fuels. They have relatively low viscosities in comparison with many high density fuels. Table 3 lists properties of fourteen selected fuels, from which a comparison of the amines of this invention to other fuels may be made. In the table, DIADAM-E is a designation for 7-(N-methyl-N-pentylamino)-1,3,5-triazaadamantane and DIADAM-12 is a designation for a mixture of DIADAM-E (82%), n-butylbenzene (10%) and toluene (8%) prepared to form a mixture melting below 25° C.

Table 3

PROPERTIES OF MISCELLANEOUS FUELS*

| Entry no. | Fuel | Density g/cc (20°) | Mp °C | Viscosity Centipoise (°C) | | $\Delta H_c$ (gross)[a] Btu/gal (obs) |
|---|---|---|---|---|---|---|
| 1 | $C_6H_{12}N_4$ (hexamine) | 1.33 | 268[b] | — | | 144,500 |
| 2 | $H_2NNHCH_2CH_2NHNH_2$ | 1.09 | 12 | 900 | (25) | 102,500 |
| 3 | $C_{14}H_{18}$ (Shelldyne-H) | 1.08 | −38 | 25 | (20) | 161,000[c] |
| 4 | $C_{10}H_{16}$ (adamantane) | 1.07 | 268[d] | — | | 170,000 |
| 5 | $C_{13}H_{26}N_4$ (DIADAM-E)[e] | 1.06 | 32–35 | — | | 138,100 |
| 6 | $C_6H_5NH_2$ | 1.02 | −6 | 4.8 | (17.4) | 133,000 |
| 7 | DIADAM-12[f] | 1.01 | 18–22 | 15.4 | (20) | 135,000 |
| 8 | $N_2H_4$ | 1.01 | 1.4 | 0.97 | (20) | 70,000 |
| 9 | $(H_2NCH_2CH_2)_2NH$ | 0.96 | −39 | 71.4 | (25) | (105,000)[g] |
| 10 | $C_6H_5NHC_2H_5$ | 0.96 | −63.5 | 204 | (25) | 132,000 |
| 11 | $H_2NCH_2CH_2NH_2$ | 0.90 | 8.5 | 1.54 | (25) | 102,000 |
| 12 | $C_6H_6$ (benzene) | 0.88 | 5.5 | 0.0095 | (26) | 132,000 |
| 13 | $(CH_3)_2NNH_2$ | 0.79 | −52 | 0.59 | (15.6) | 87,500 |
| 14 | JP-4 | 0.75 | −54 | 5 | (−65) | 117,500[c] |

[a]Gross values based on a combustion at constant volume (25° C), the final combustion products consisting of liquid water and gaseous carbon dioxide and nitrogen.
[b]Sublimes at this temperature (1 atm.).
[c]Net values based on a combustion at constant pressure (1 atm., 25° C), the final combustion products consisting of gaseous water, carbon dioxide and nitrogen.
[d]Mp. in sealed tube; sublimes at 205° (1 atm.).
[e]7-(N-methyl-N-pentylamino)-1,3,5-triazaadamantane.
[f]Mixture of 7-(N-methyl-N-pentylamino)-1,3,5-triazaadamantane (82%), n-butylbenzene (10%) and toluene (8%). The number designations of the DIADAM fuels are arbitrary and correspond to specific mixtures.
[g]Calculated value.
*Some of the data in the table came from B. Kit and D. S. Evered. Rocket Propellant Handbook. New York, The Macmillan Company, 1960.

It will be noted from Table 3 that DIADAM-12 has a relatively low viscosity (15.4 centipoise at 20° C) in comparison to certain other high density amines. For example, ethylene dihydrazine (entry 2) has a viscosity of 900 centipoise at 25° C. Hydrogen bonding contributes to the viscosities of amines containing NH groups. These groups are absent in the amines of this invention. Further, tertiary amines are generally more stable than primary and secondary amines and are less sensitive to air oxidation.

Since the amines of this invention are soluble in a wide variety of hydrocarbon solvents, solutions containing one or more of the amines and one or more hydrocarbons can be made up and used as liquid fuels. The amines of this invention are also mutually soluble in polar solvents such as water, alcohols and other amines including hydrazine, and these may be used as diluents to prepare suitable fuel mixtures. The amines of this invention can also, of course, be used as solid fuels.

Table 4 lists calculated densities and heats of combustion for the 7-(N-methyl-N-alkylamino)-1,3,5-triazaadamantanes prepared.

Table 4

| Cpd | R | Density g/cc (20° C) Calcd. | Molecular Formula | Molecular Weight | Heat of Combustion Btu/gal Calcd.[b] |
|---|---|---|---|---|---|
| 4a | $CH_3$ | 1.18 | $C_9H_{18}N_4$ | 182.27 | 138,300 |
| 4b | $C_2H_5$ | 1.15 | $C_{10}H_{20}N_4$ | 196.29 | 137,700 |
| 4c | $n\text{-}C_3H_7$ | 1.12 | $C_{11}H_{22}N_4$ | 210.32 | 138,400[c] |
| 4d | $n\text{-}C_4H_9$ | 1.10 | $C_{12}H_{24}N_4$ | 224.34 | 138,200 |
| 4e | $n\text{-}C_5H_{11}$ | 1.08 | $C_{13}H_{26}N_4$ | 238.37 | 138,600[d] |
| 4f | $n\text{-}C_6H_{13}$ | 1.06 | $C_{14}H_{28}N_4$ | 252.40 | 138,600 |

[a]Observed density values are listed in Table 2.
[b]Calculated from the summation of bond energy increments, e.g., C-N, 27.412; C-C, 48.019; C-H, 52.634; N-H, 25.925; N-N, 19.809 cal/g mole and the equation: $\Delta H_c = (\Sigma \text{ bond increments})(d)(1.504/\text{mol. wt.})$. These values are gross values based on a combustion at constant volume (25° C), the final combustion products consisting of liquid water, gaseous carbon dioxide and nitrogen.
[c]Measured value 135,000 Btu/gal.
[d]Measured value 138,100 Btu/gal.

Judging from the work carried out, it would appear that 7-(N-methyl-N-alkylamino)-1,3,5-triazaadamantanes having alkyl groups other than those actually utilized could readily be prepared using similar reactions. It will also be realized by those skilled in the art that it might be perfectly feasible to vary the conditions, e.g., times, pressures, etc., used in the foregoing specific examples somewhat and still achieve excellent results.

I claim:

1. A compound represented by the formula:

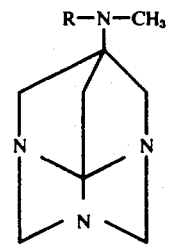

wherein R is an alkyl selected from the group consisting of $C_2H_5$, $C_3H_7$, $C_4H_9$, $C_5H_{11}$, $C_6H_{13}$, and $C_7H_{15}$.

2. A method for preparing 7-(N-methyl-N-alkylamino)-1,3,5-triazaadamantanes comprising the steps of:

1. preparing 7-nitro-1,3,5-triazaadamantane by adding nitromethane and paraformaldehyde to a refluxing solution of ammonium acetate in ethanol;

2. preparing 7-amino-1,3,5-triazaadamantane by reacting 7-nitro-1,3,5-triazaadamantane with hydrogen in the presence of a rhodium-charcoal catalyst;
3. preparing 7-(N-alkylamino)-1,3,5-triazaadamantane by reacting 7-amino-1,3,5-triazaadamantane with an aldehyde and hydrogen in the presence of a platinum catalyst; and
4. preparing the final product by reacting 7-(N-alkylamino)-1,3,5-triazaadamantane with formaldehyde and hydrogen in the presence of a nickel catalyst.

* * * * *